US008891848B2

(12) United States Patent
Blumfield et al.

(10) Patent No.: US 8,891,848 B2
(45) Date of Patent: Nov. 18, 2014

(54) AUTOMATED VERTEBRAL BODY IMAGE SEGMENTATION FOR MEDICAL SCREENING

(75) Inventors: Anthony Blumfield, Scarsdale, NY (US); Einat Blumfield, Scarsdale, NY (US)

(73) Assignee: Radnostics, LLC, Scarsdale, NY (US)

( * ) Notice: Subject to any disclaimer, the term of this patent is extended or adjusted under 35 U.S.C. 154(b) by 449 days.

(21) Appl. No.: 13/412,736

(22) Filed: Mar. 6, 2012

(65) Prior Publication Data
US 2013/0077840 A1    Mar. 28, 2013

Related U.S. Application Data

(60) Provisional application No. 61/496,710, filed on Jun. 14, 2011.

(51) Int. Cl.
| | |
|---|---|
| *G06K 9/00* | (2006.01) |
| *G06K 9/34* | (2006.01) |
| *A61B 6/00* | (2006.01) |
| *G06F 19/00* | (2011.01) |

(52) U.S. Cl.
CPC .............. *G06K 9/34* (2013.01); *G06F 19/321* (2013.01)
USPC ........... 382/131; 382/128; 382/132; 382/173; 382/275; 600/594

(58) Field of Classification Search
CPC ........ G06K 9/34; G06T 5/002; G06T 7/0012; G06T 7/0087; G06T 7/0091; G06T 7/0079; G06T 2207/10072; G06T 2207/10081; G06T 2207/20128; G06T 2207/30012; A61B 6/505; A61B 6/5217; A61B 5/4509
USPC ........... 382/131, 128, 132, 173, 275; 600/594
See application file for complete search history.

(56) References Cited

U.S. PATENT DOCUMENTS

| | | | | |
|---|---|---|---|---|
| 4,723,557 | A * | 2/1988 | Gross | 600/594 |
| 5,835,619 | A * | 11/1998 | Morimoto et al. | 382/132 |
| 6,608,917 | B1 * | 8/2003 | Wei et al. | 382/132 |
| 6,839,457 | B1 * | 1/2005 | Azuma et al. | 382/131 |
| 8,139,829 | B2 * | 3/2012 | Goto et al. | 382/128 |
| 8,437,521 | B2 * | 5/2013 | Lu et al. | 382/128 |

(Continued)

OTHER PUBLICATIONS

Kyriakou, et al. "Image-based online correction of misalignment artifacts in Cone-Beam CT." Medical Imaging. (2009): 1-10. Print.*

(Continued)

*Primary Examiner* — Michael A Newman
(74) *Attorney, Agent, or Firm* — McCarter & English, LLP

(57) ABSTRACT

A method is disclosed for fully automated segmentation of human vertebral body images in a CT (computerized tomography) study with no user interaction and no phantoms, which has resiliency to anatomical abnormalities, and protocol and scanner variations. The method was developed to enable automated detection of osteoporosis in CT studies performed for other clinical reasons. Testing with 1,044 abdominal CTs from multiple sites, resulted in detection of 96.3% of the vertebral bodies and 1% false positives. Of the detected vertebral bodies, 83.3% were segmented adequately for sagittal plane quantitative evaluation of vertebral fractures indicative of osteoporosis. Improved results were observed when selecting the best sagittal plane of 3 for each vertebra, yielding a segmentation success rate of 85.4%. The method is preferably implemented in software as a building block in a system for automated osteoporosis detection.

7 Claims, 14 Drawing Sheets

(56) References Cited

U.S. PATENT DOCUMENTS

| | | | |
|---|---|---|---|
| 2002/0061126 A1* | 5/2002 | Gerard et al. | 382/128 |
| 2003/0099385 A1* | 5/2003 | Zeng et al. | 382/128 |
| 2006/0251302 A1* | 11/2006 | Abufadel et al. | 382/128 |
| 2007/0076932 A1* | 4/2007 | Blumhofer | 382/128 |
| 2008/0037843 A1* | 2/2008 | Fu et al. | 382/128 |
| 2008/0044074 A1* | 2/2008 | Jerebko et al. | 382/128 |
| 2011/0064291 A1* | 3/2011 | Kelm et al. | 382/131 |
| 2011/0116697 A1* | 5/2011 | Dafni et al. | 382/131 |
| 2012/0143090 A1* | 6/2012 | Hay et al. | 600/587 |

OTHER PUBLICATIONS

Genant, et al. "Advanced CT bone imaging in osteoporosis." Rheumatology. 47. (2008): iv9-iv16. Print.*

Nishihara, et al. "Evaluation of osteoporosis in X-ray CT examination: A preliminary study for an automatic recognition algorithm for the central part of a vertebral body using abdominal X-ray CT images." Computerized Medical Imaging and Graphics. 29. (2005): 259-266. Print.*

Kindler, et al. "Automated model-based vertebra detection, identification, and segmentatioin in CT images." Medical Image Analysis. 13. (2009): 471-482. Print.*

Asian, et al. "3D Vertebrae segmentation in CT images with random noises." International Conference on Pattern Recognition. (2010): 2290-2293. Print.*

Kim, et al. "A fully automated vertebra segmentation method using 3D deformable fences." Computerized Medical Imaging and Graphics. 33. (2009): 343-352. Print.*

Rangayyan, et al. "Method for the automatic detection and segmentation of the spinal canal in computed tomographic images." Journal of Electronic Imaging. 15.3 (2006): 1-9. Print.*

Carbadillo-Gamio, et al. "Normalized cuts in 3-D for spinal MRI segmentation." IEEE Transactions on Medical Imaging. 23.1 (2004): 36-44. Print.*

* cited by examiner

 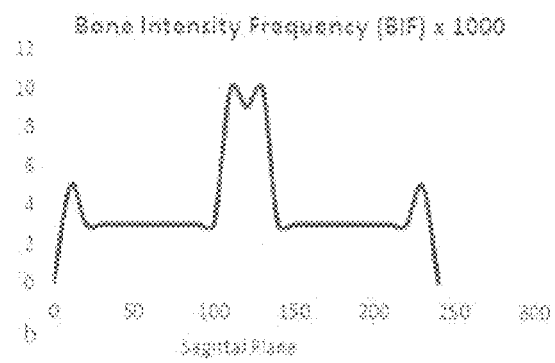
Fig. 5a                Fig. 5b
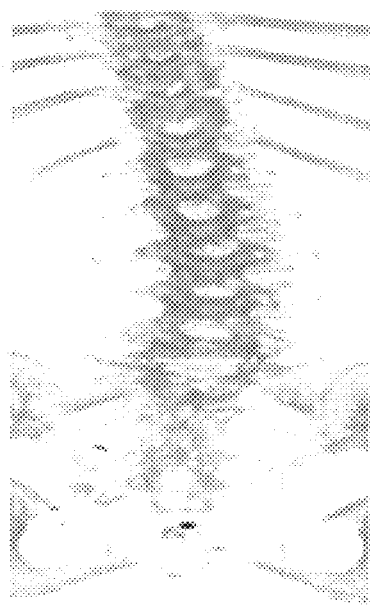 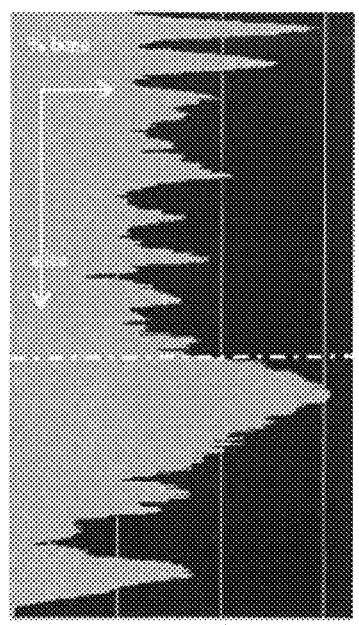
Fig. 6a         Fig. 6b

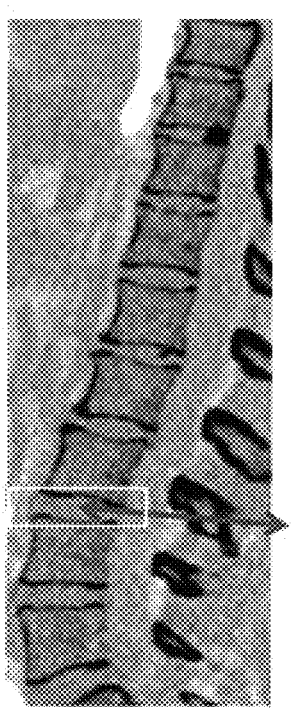
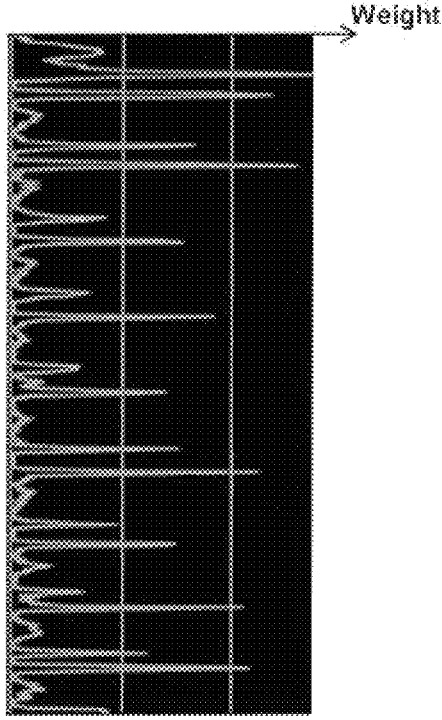
Fig. 13a    Fig. 13b
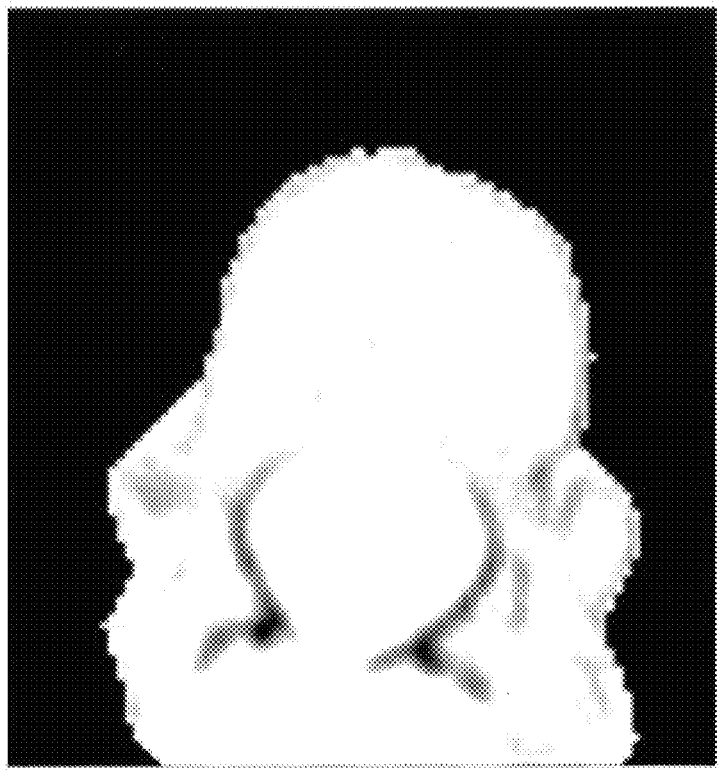
Fig. 14

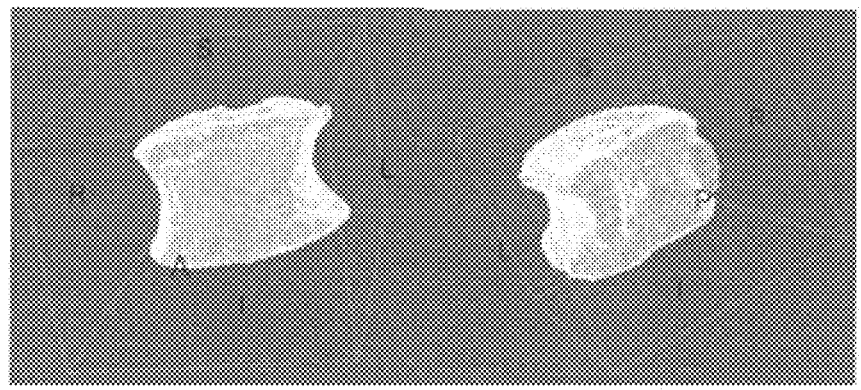
Fig. 21
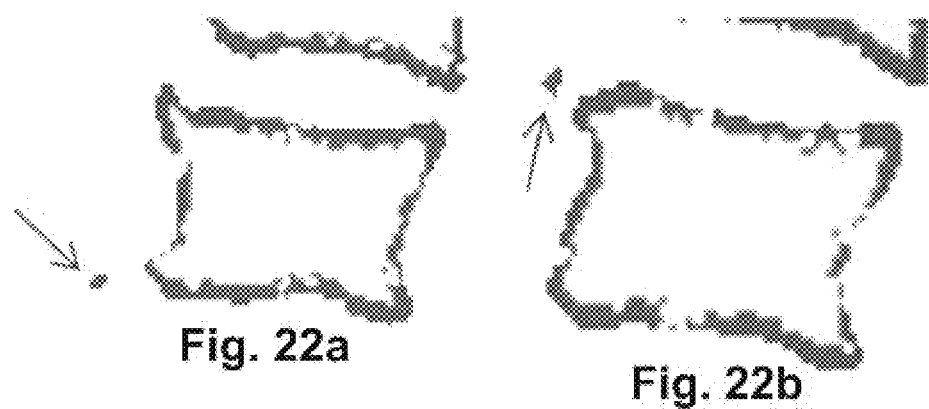
Fig. 22a
Fig. 22b
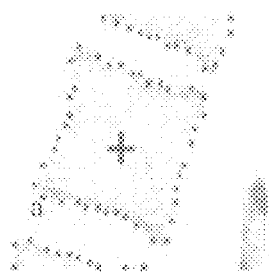
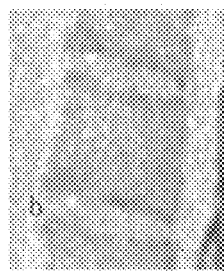
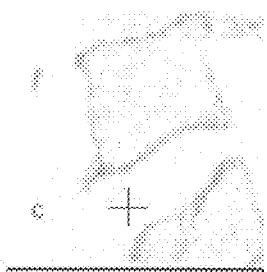
FIG. 23a
FIG. 23b
FIG. 23c

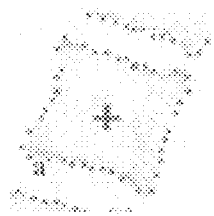 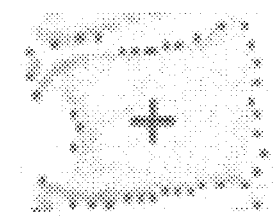
Fig. 24a  Fig. 24b
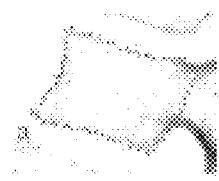 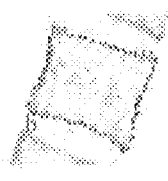 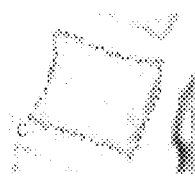 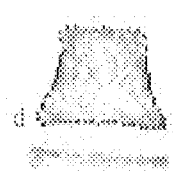
Fig. 25a  Fig. 25b  Fig. 25c  Fig. 25d
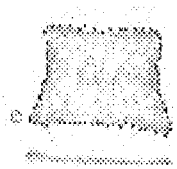 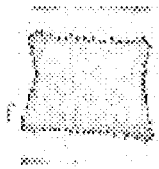 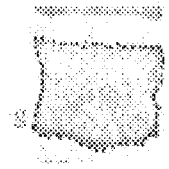 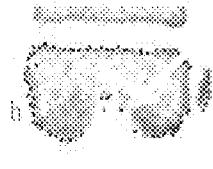
Fig. 25e  Fig. 25f  Fig. 25g  Fig. 25h

AUTOMATED VERTEBRAL BODY IMAGE SEGMENTATION FOR MEDICAL SCREENING

CROSS REFERENCES

This application is a nonprovisional of U.S. Provisional Application Ser. No. 61/496,710, filed Jun. 14, 2011, entitled "AUTOMATED VERTEBRAL BODY SEGMENTATION," the disclosure of which application is hereby incorporated by reference herein in its entirety.

BACKGROUND OF THE INVENTION

The present invention relates generally to computerized medical systems for diagnosing the human body and, more particularly, concerns procedures for analyzing images of a volume containing the spine to isolate the spine from its surroundings and to isolate the various components of the spine.

Osteoporosis is a condition of decreased bone mass that leads to fractures and negatively impacts millions of people, causing immobility, pain, and mortality, and costing billions of dollars annually. Although an effective technique (DXA) for early diagnosis exists and the condition is treatable, screening compliance is low. Preliminary diagnosis of osteoporosis is achievable by inspecting vertebral bodies in images, usually CT scans performed for other clinical reasons, based on morphology, structure, and density. However, this is time consuming and the condition is frequently under diagnosed.

Diagnosis involves segmentation of the spine images to identify and isolate the various components of the spine. In most clinical settings spine segmentation is a manual operation performed by a trained radiologist. This methodology is not amenable to quantitative anatomical analysis and relies upon the radiologists experience to identify abnormalities in imaging studies. In cases where quantitative analysis on a spine is performed, the segmentation process is typically manual or semi-automatic and requires user intervention in various stages of the segmentation, such as spine region isolation, seed positioning and iterative refinements.

A process is needed to detect osteoporosis findings in CT scans. As the number of CTs performed in a medical setting is typically large the process should be fully automated. As the CTs are not performed specifically for osteoporosis detection, no additional, constraints may be imposed (i.e. there is no ability to add phantoms to the scan). In addition, die process should be resilient to imaging protocol variations and anatomical variations and abnormalities.

In order to perform automated quantitative analysis of the vertebral body, a segmentation building block is required that accepts a CT study as input and produces a segmentation of the vertebral bodies as output. Challenges in vertebral body segmentation result from variable input data caused by anatomical abnormalities and variations, study protocol and scanner. Examples, of anatomical abnormalities and variations include low density vertebral cortex, fatty trabecular bone, vascular calcifications osteophytes, scoliosis, calcified longitudinal ligaments, prominent epidural veins, focal disc calcifications, and noise enhancers such as obesity and metal hardware. Examples of study protocol variations include contrast in the vascular and digestive systems and patient position and orientation. Examples of scanner variations include radiation dose, resolution, and scanner table artifacts.

In accordance with one aspect of the invention, a computerized system receives as input a digital representation of a volume region of a patient's body containing the spine. Typically, but not necessarily, the representation is in the form of a three-dimensional DICOM or MHA representation of a CT imaging study. The system analyzes the volume using statistical, heuristic and other computational techniques, isolates the spine from the surrounding volume, and segments each vertebral body trabecular bone, each vertebral body cortex, each intervertebral disc, and locates the planes of the intervertebral discs. A label map is produced that corresponds to the input volume and classifies each voxel, as either background or as part of a specified spine element.

A system in accordance with the present invention provides fully automated vertebral body segmentation, eliminating the labor intensive portions of the segmentation process and enabling a broad range of clinical and research scenarios which were previously limited by the availability of trained professionals to perform the segmentation. As an example, it makes possible the screening of large quantities of imaging studies using quantitative analyses of the automatically generated vertebral segmentations produced in accordance with the present invention.

BRIEF DESCRIPTION OP THE DRAWINGS

The foregoing description and further objects, features and advantages of the present invention will be understood more completely from the following detailed description of a presently preferred, but nonetheless illustrative, embodiment in accordance with the present invention, with reference being had to the accompanying drawings, in which.

Figure 3:
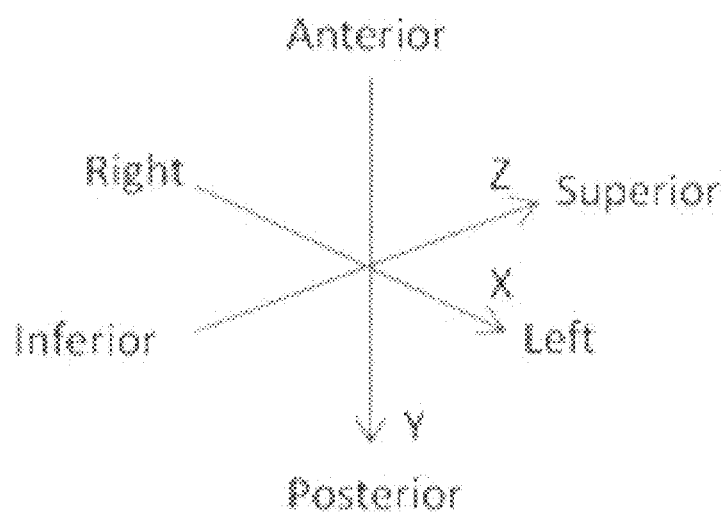
Figures 8A, 8B, 8C:
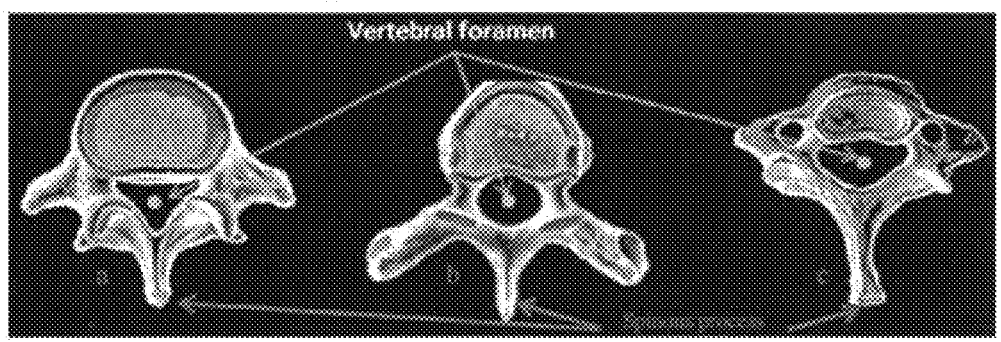
Figure 9:
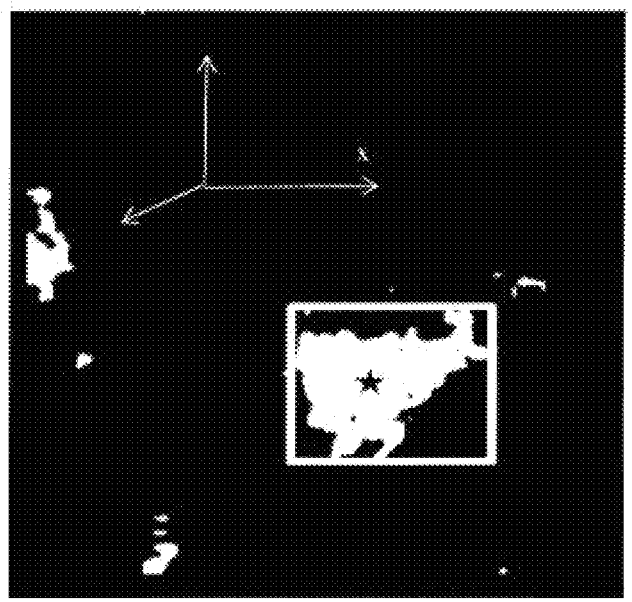
Figure 10:
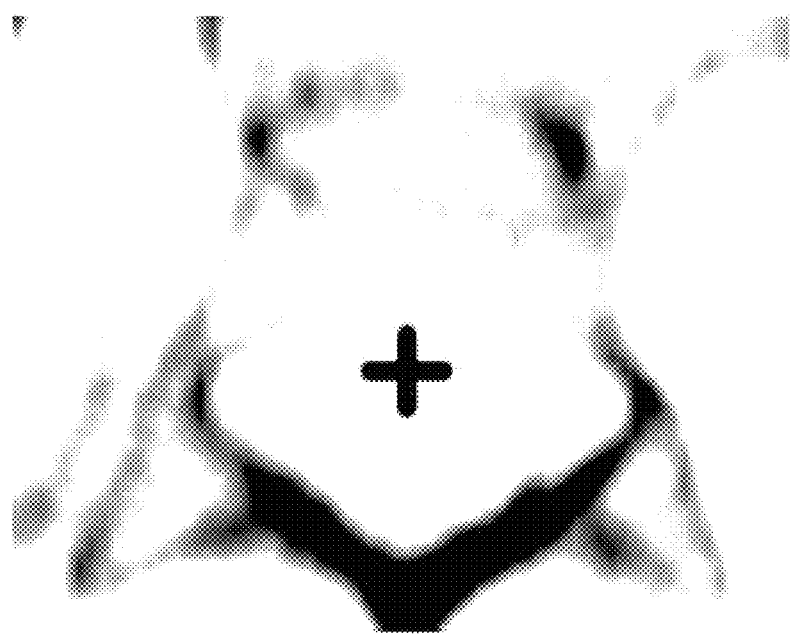
Figure 11:
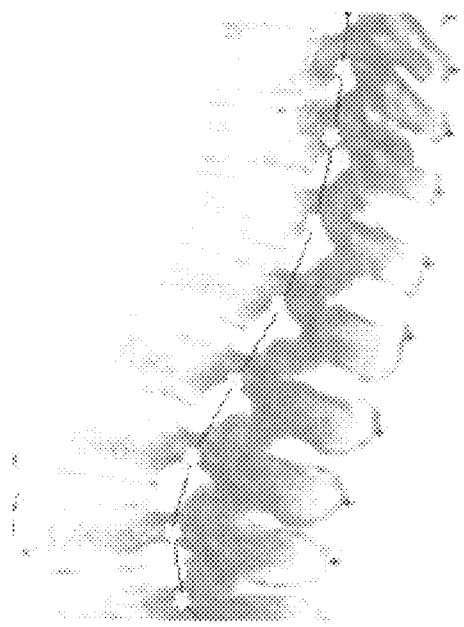
Figure 15:
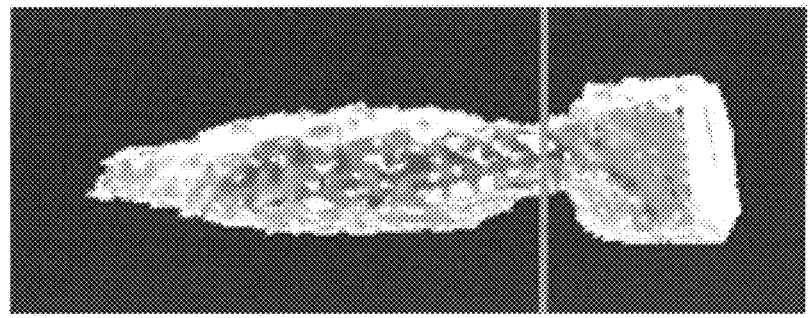
Figure 16:
Figure 17:
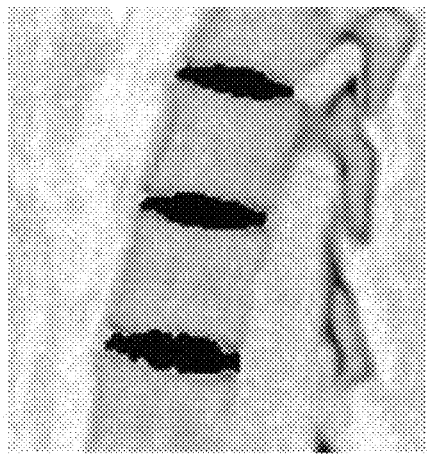
Figure 18:
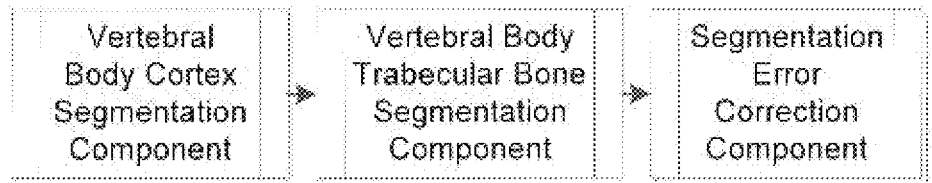
Figure 19:
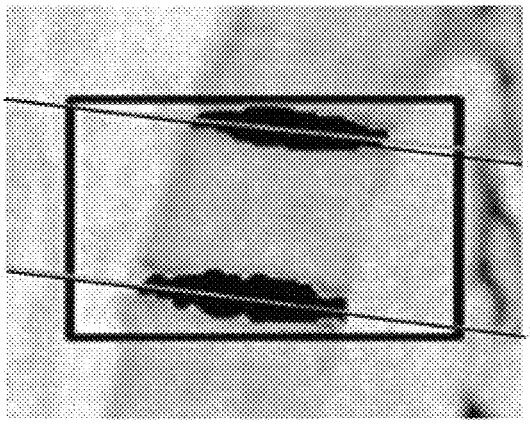
Figure 20:
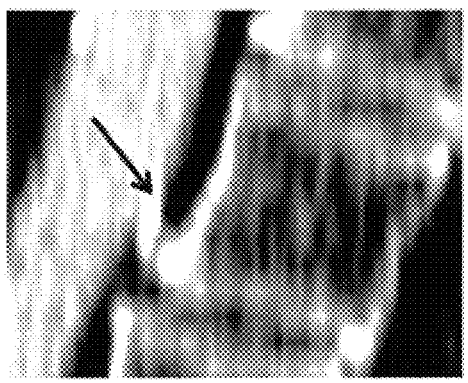
Figure 26A:
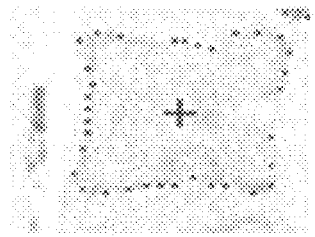
Figure 26B:
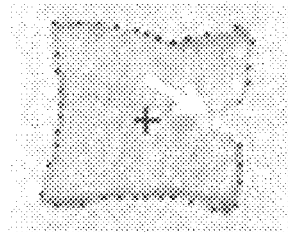
Figure 26C:
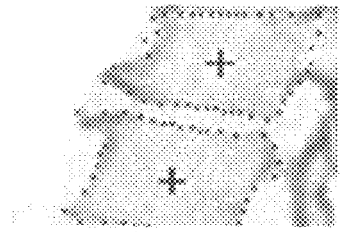
Figure 26D:
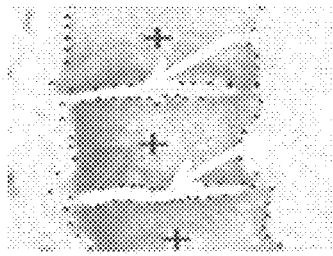
Figure 26E:
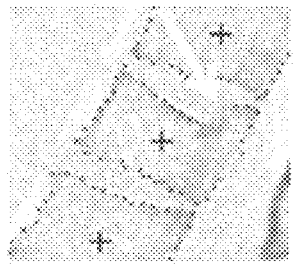
Figure 26F:
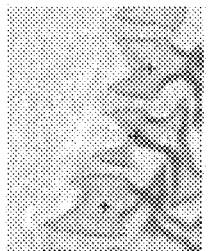
Figure 26G:
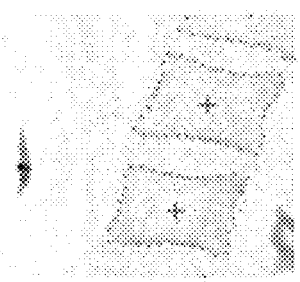
Figure 26H:
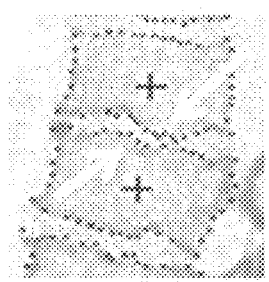
Figure 26I:
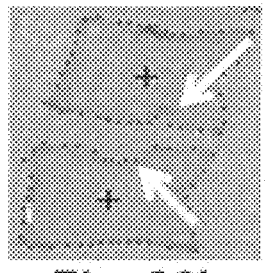
Figure 26J:
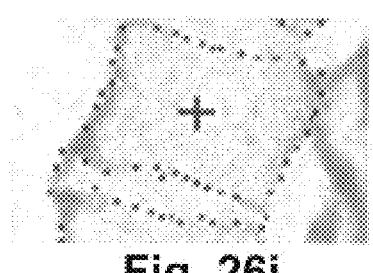
Figure 27A:
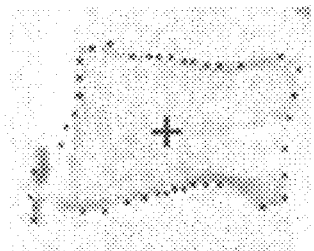
Figure 27B:
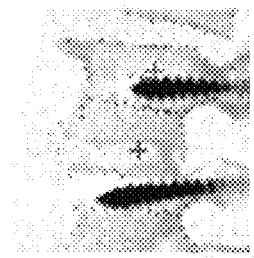
Figure 27D:
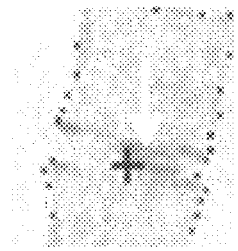
Figure 27D:
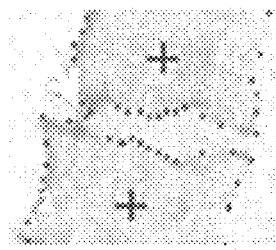
Figure 27D:
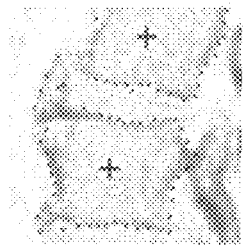
Figure 27E:
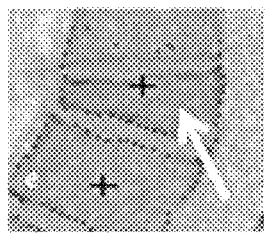
Figure 27F:
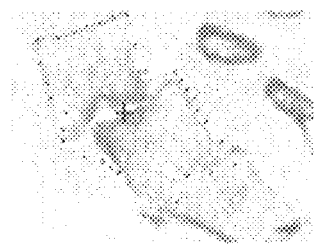
Figure 28:
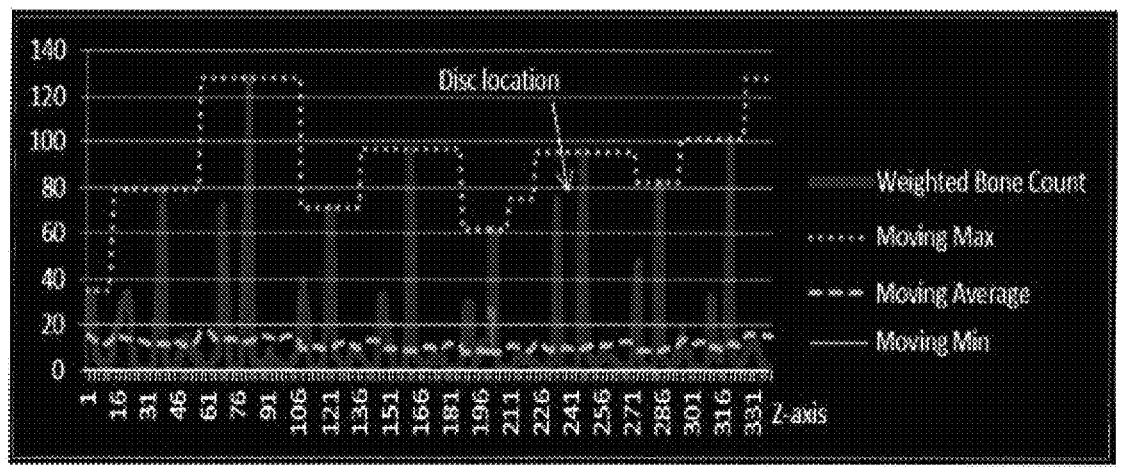

FIG. 3 defines the Cartesian coordinate system that will be used throughout this description;

FIG. 4; (a) illustrates artifacts of the CT machine, the CT scanner table and mattress in an axial slice of an abdominal CT study; and (b) is a graph of Entropy E(y) of the CT study with cutoff planes used to crop the patient's body;

FIG. 5; (a) shows the isolated abdominal CT coronal plane and (b) shows a corresponding graph of relative frequencies of skeletal voxels on sagittal planes, the shaded area marking the region of the spine;

FIG. 6: (a) illustrates a max intensity coronal projection of an abdomen-pelvis CT study and (b) is a corresponding bar graph of horizontal bone frequency;

FIG. 7: (a) illustrates the most posterior high density vertex on a sample axial plane, (b) is a sagittal, view of the posterior vertices along a sample spine segment using a max intensity filter, and (c) shows the spinous process polyline connecting the process tips presented in a max intensity filter of a spine;

FIG. 8 is an axial view of typical morphologies of vertebral foramina in the spinal canal: (a) lumber, (b) thoracic, (c) cervical;

FIG. 9 is a binary map of intensity frequencies along the Z-axis, with III) values typical of the spinal canal, as compared to a threshold;

FIG. 10 shows the isolated vertebral foramen;

FIG. 11 shows the spinal canal seeds (white stars) and the spinal canal polyline;

FIG. 12: (a) shows a rectangular parametric curve along the estimated center of the vertebral bodies, b-cross section of the parametric curve used for weight analysis and (b) shows the cross section of the parametric curve used for weight analysis;

FIG. 13: (a) shows a sagittal reconstruction of the CT study and, alongside, (b) shows a plot of Weight (SC), the black arrow showing the correlation between an intervertebral disc and a dip between two spikes in the plot;

FIG. 14 is an axial slice of the abdomen CT, showing an intervertebral disc where all tissues on the anterior, left, and right have been removed using a flexible surface;

FIG. 15 shows a lentiform shaped intervertebral disc, with a posterior bulge into the spinal canal which is removed from the disc region at the vertical line;

FIG. 16 shows An intervertebral disc with superior and inferior planes orthogonal to the spinal, canal polyline in the vicinity of the adjacent vertebral bodies' cortex;

FIG. 17 shows the intervertebral discs marked in white in a sagittal max intensity projection:

FIG. 18 is a flowchart describing the workflow of the vertebral body segmentation system that delineates the trabecular bone and cortex of each vertebral body;

FIG. 19 shows a cuboid region encasing vertebra and both adjacent disks with posterior and anterior margins;

FIG. 20 is a CT demonstrating calcification in the aorta in the vicinity of the vertebral body;

FIG. 21 shows two three-directional views of vertebra region Rv in its cuboid region Cv (wireframe) after restricted voxels are removed;

FIGS. 22(a) and 22(b) show samples of islands marked as cortex in a label map of cortex and trabecular bone;

FIG. 23 shows a vertebra center: (a) detected—marked with a white cross, (b) undetected, and (c) false positive—marked with a white cross;

FIG. 24 shows cortex morphology segmentation marked with white, dots: (a) pass, (b) fail;

FIG. 25 shows multi-plane vertebral body morphology segmentation denoted with white dotted outlines: (a) right sagittal plane, (b) mid sagittal plane, (c) left sagittal plane, (d) anterior coronal plane, (e) mid-anterior coronal plane, (f) mid coronal plane, (g) mid-posterior coronal plane, (h) posterior coronal plane with epidural vein marked with an arrow;

FIG. 26 shows image variation resiliency samples: (a) calcification of the aorta, (b) epidural vein, (c) ostiophytes, (d) narrow disc with vacuum phenominon, (e) vertebral, fracture, (f) scoliosis, (g) contrast in colon, (h) endplate irregularity, (i) schmorl nodes, (j) calcified anterior longitudinal ligament;

FIG. 27 shows image variation failure samples: (a) aorta calcification mistaken as cortex, (b) metal screws cause incorrect segmentation), (c1) and (c2) disc calcification causes incorrect segmentation, (d) calcified anterior longitudinal ligament causes incorrect segmentation, (e) incorrect segmentation of fractured vertebral body, (f) spondylolisthesis causing detection failure; and FIG. 28 illustrates the results of a statistical analysis to detect intervertebral disc planes.

DETAILED DESCRIPTION

For better organization the description is broken down into subsections related to different portions of the system.

Vertebral Body Segmentation

Figure 1:
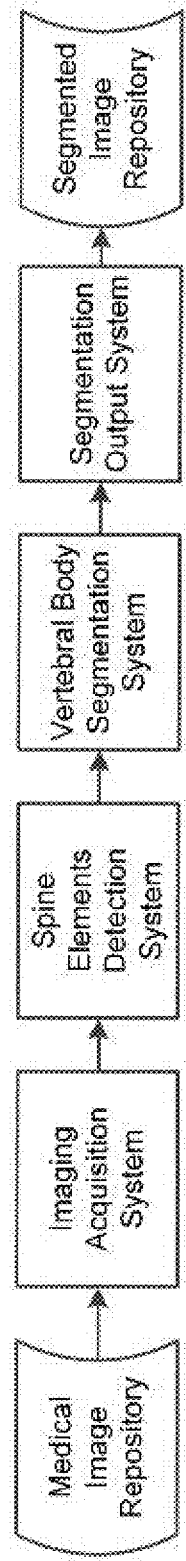
FIG. 1 is a block diagram illustrating the high level workflow of the software pipeline developed to implement automated vertebral body segmentation.

FIG. 1 is a block diagram illustrating the high, level workflow of the software pipeline developed to implement automated vertebral body segmentation. The imaging acquisition system retrieves the CT study from the medical image repository (e.g. the PACS system) and the spine elements detection system identifies the location of the spine elements in the study images. Next, the vertebral body segmentation system labels the cortex and the trabecular bone of each vertebral body. Finally, the segmentation output system stores the results in the segmented image repository (e.g. a hard drive).

Spine Element Detection System

Figure 2:
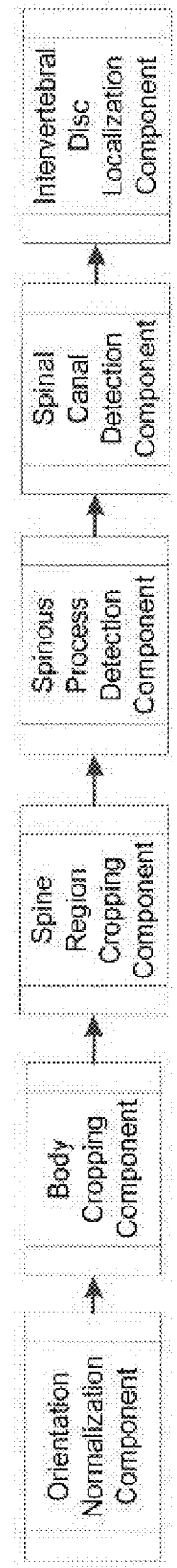
FIG. 2 is a flow chart illustrating the workflow of die spine elements detection system of FIG. 1.

FIG. 2 is a flow chart illustrating the workflow of the spine elements detection system of FIG. 1, which isolates the spine region and detects the spinal canal and intervertebral discs in the CT study.

Orientation Normalization Component

Based on Meta data in the CT study, the study orientation is normalized to the standard coordinate system shown in FIG. 3.

Body Cropping Component

Figure 4A:
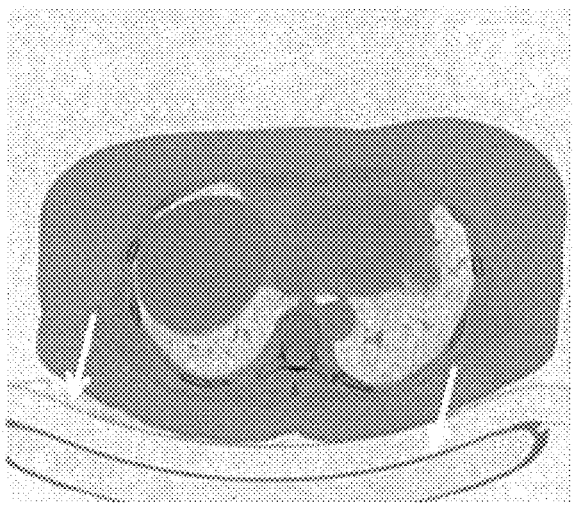
Figure 4B:
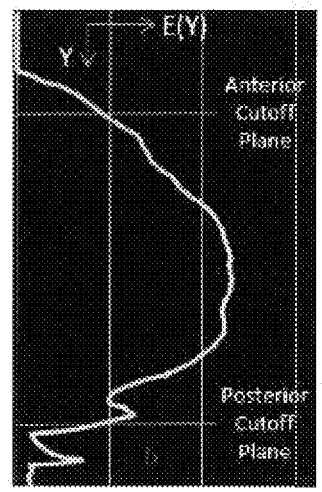

The CT study may include artifacts of the CT machine such, as the mattress and table seen in FIG. 4(a). Typically these structures have lower entropy along the Z-Axis as compared to the human body and a linear entropy algorithm is applied to remove them. This process also removes the empty planes surrounding the patient. The average Shannon entropy, defined in Equation (1) and illustrated in FIG. 4(b), is calculated for each coronal plane and used to determine the anterior and posterior cutoff planes and exclude the low entropy planes above and below the patient.

$$E(y) = \frac{\sum_{x=L}^{Nx} H(x, y)}{Nx} \quad (1)$$

where:

$N_x$ is the number of sagittal planes and $H(x,y)$ is the Shannon entropy of the distribution of density classes along the Z-axis, at location (x,y). Density classes are defined in Table and group regions of HU (Hounsfield Units) values in the CT study. E.g. HU values in the range (−10,10], typical of water, are grouped into density class 6.

TABLE 1

Map of HU (Hounsfield Units) values to density classes for Shannon entropy analysis

| Density Class | HU value greater than | HU value less equal to |
|---|---|---|
| 1 (air) | −infinity | −600 |
| 2 (lung) | −600 | −400 |
| 3 | −400 | −100 |
| 4 (fat) | −100 | −50 |
| 5 | −50 | −10 |
| 6 (water) | −10 | 10 |
| 7 | 10 | 40 |
| 8 (soft tissue) | 40 | 80 |
| 9 | 80 | 300 |
| 10 (bone) | 300 | 1100 |
| 11 | 1100 | Infinity |

For patients in the prone position the posterior planes are not removed using this method to avoid clipping spinous processes when patients are not entirely horizontal. To remove the sagittal planes to the left and right of the patient's body, the same method is used interchanging x and y.

Spine Region Cropping Component

Additional anterior cropping is accomplished by removing the front ⅓ of the coronal planes from the study, eliminating a large portion of the anterior rib cage and soft tissues anterior to the spine. Additional left and right, cropping is accomplished by isolating the middle sagittal planes with a high bone intensity frequency (BIF) as defined in Equation (2) and illustrated in FIG. 5, where (a) shows the isolated abdominal CT coronal plane and (b) shows a corresponding graph of relative frequencies of skeletal voxels on sagittal planes, the shaded area marking the region of the spine.

$$\text{Map}(x, y) = \begin{bmatrix} 1, & \text{frequency } (-50 \text{ hu} < \text{Intensity } (x, y, z) < 50 \text{ hu}, Z\text{tmin} < z < Z\text{tmax} > 50\% \\ 0, & \text{otherwise} \end{bmatrix} \quad (3)$$

$$\text{BIF}(x) = \text{Relative Frequency}\{\text{Intensity}(x,y,z) > 100 \text{ hu}, (y,z) \in \text{sagittal plane}(x)\} \quad (2)$$

Inferior cropping removes the axial slices below the upper pelvic border line shown in FIG. 6 by analyzing the horizontal bone intensity frequency (>300 hu) on a 2D maximum intensity coronal projection. In FIG. 6, (a) illustrates a max intensity coronal projection of an abdomen-pelvis CT study, the pelvis cutoff plane being marked with a dashed line; and (b) is a corresponding bar graph of horizontal, bone frequency, demonstrating increase in frequency in the vicinity of the pelvis. Note that vertebra L5 might be removed in this process. This is consistent with some (but not all) quantitative techniques for osteoporosis detection that inspect through L4 only.

Spinous Process Detection Component

The tips of the spinous processes are used as markers. Their level of variation is typically inconsequential: their high density is distinct from their surroundings; and they are distant from structures subject to image study variations (such as contrast in the vascular and digestive systems).

Figure 7A:
Figure 7B:
Figure 7C:

To locale the spinous process tips, the center sagittal planes are analyzed and the most posterior voxel with high density on each axial plane is recorded as demonstrated by the white arrow in FIG. 7(a), illustrating the most posterior high density vertex on a sample axial plane. These voxels create a series of vertices that contour the posterior of the spine as shown, by the white dotted line in FIG. 7(b), a sagittal view of the posterior vertices along a sample spine segment using a max intensity filter. Each vertex is inspected and removed if there is another vertex posterior to it and within a distance equal to the typical low end gap between spinous processes in the adult human body. Next, redundant vertices on the same tip are removed by uniting vertices whose connecting line passes mostly through high density voxels. Finally erroneous process tips, resulting from posterior rib bone, are eliminated by requiring tips to be vertically aligned within a tolerance sufficient to account for scoliosis. The polyline connecting the spinous process tips is called the spinous process polyline and its end segments are extended to the boundaries of the image as shown in FIG. 7(c), which shows the spinous process polyline connecting the process tips presented in a max intensity filter of a spine.

Spinal Canal Defection Component

To detect the spinal canal, we use the spinous process tips to find the locations of the vertebral foramina in the center of the canal as shown in FIG. 8, an axial view of typical morphologies of vertebral foramina in the spinal canal: (a) lumber, (b) thoracic, (c) cervical. For each spinous process tip ($x_t$, $y_t$, $z_t$) we define a cuboid $C_t[(x_t-25 \text{ mm}, y_t-80 \text{ mm}, z_t), (x_t+25 \text{ mm}, y_t-10 \text{ mm}, z_t+30 \text{ mm}]$ that encases the spinal canal region based on typical adult anatomical dimensions and apply a neighborhood mean filter (R=1) for noise reduction. We then create a binary map as defined in Equation (3) and illustrated in FIG. 9, showing the areas on the (x,y) plane of cuboid $C_t$, which have a high count of voxels along the Z-axis within the density range of the spinal canal (−50 hu, 50 hu).

FIG. 9 is a binary map of intensity frequencies along the Z-axis, with HI) values typical of the spinal canal as compared to a threshold. White pixels are denoted as "1" and represent areas with high voxel counts.

Next, the binary map is analyzed starting from the center and spiraling outward. For representative points on the spiral, a surrounding shape composed of values of "1" is created using a flood fill algorithm. The shape is analyzed for size and morphology comparable to the vertebral foramina in FIG. 8. Morphology analysis is based on the aspect ratio of the encasing rectangle as compared to samples, and the occupation ratio of "1"s inside the rectangle (see sec FIG. 9. The center of gravity of the "1"s in the first shape in the spiral that meets the size and shape criteria is taken as the center of the foramen ($X_c$, $Y_c$) as illustrated by a black star in FIG. 9.

Next, for each axial plane in cuboid $C_t$, a 2D shape consisting of voxels with intensity values typical of the spinal canal is created using a flood fill algorithm seeded with ($X_c$, $Y_c$). The axial plane ($Z_c$) with the smallest shape in diameter is marked as the plane of the vertebral foramen, and its center ($X_c$, $Y_c$, $Z_c$) is marked as a spinal canal seed shown in FIG. 10. A spinal canal polyline is created by connecting the spinal canal seeds ($X_c$, $Y_c$, $Z_c$). Seeds in close proximity are united and seeds whose adjacent segments both cross through skeletal tissue are removed from the polyline. Next, outlier seeds are removed using linear regression, while allowing for cases of scoliosis. Finally the polyline is extended to the image boundary as illustrated in FIG. 11, showing the spinal canal seeds with white stars and the canal polyline.

Intervertebral Disc localization Component

Figures 12A, 12B:
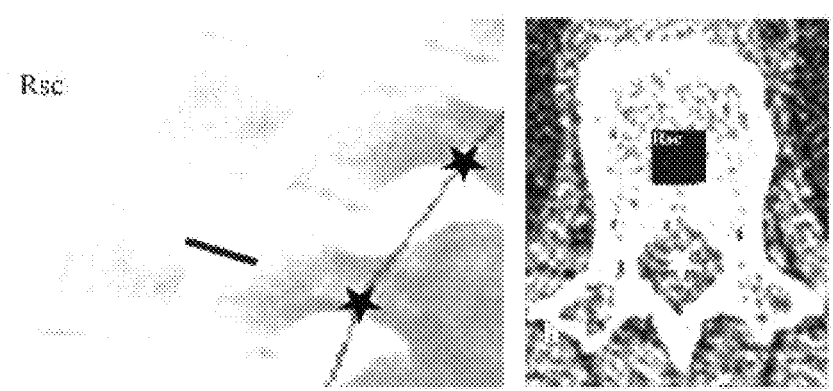

Localizing the regions of the intervertebral discs facilitates the detection of the vertebral bodies. To localize the discs, a rectangular parametric curve is positioned along the expected centers of the vertebral bodies, based on typical vertebrae, dimensions, as shown by the shaded area in FIG. 12(a), showing a rectangular parametric curve along the estimated center of the vertebral bodies, FIG. 12(b) shows the cross section of the parametric curve used for weight analysis. The cross sections, Rsc, are inspected and weights are calculated, using Equation 4, to produce higher values for cortex and lower values for discs. The weights are then plotted along the Z-axis as shown in FIG. 13 and the plot is analyzed to detect the relative dips and peaks revealing the locations of the intervertebral discs and adjacent vertebral body cortex. FIG. 13(a) shows a sagittal reconstruction of the CT study and alongside, in FIG. 13(b), a plot of Weight(SC). The black arrow shows the correlation between an intervertebral disc and a dip between two spikes in the plot.

$$\text{Weight}(sc) = \text{Frequency}(200 \text{ hu} \leq \text{Intensity} < 400 \text{ hu}) + 4 * \text{Frequency}(\text{Intensity} \leq 400 \text{ hu}) \quad (4)$$

To localize each disc, a cuboid region, $C_d$, is created encasing the vicinity of the disc and the adjacent vertebral bodies' cortex as illustrated by the white rectangle in FIG. 13. The cuboid is restricted by attaching flexible surfaces to the left, right, and anterior of the disc and removing all voxels outside the flexible surfaces as shown in FIG. 14, which is an axial slice of the abdomen CT, showing an intervertebral disc where all tissues on the anterior, left, and right, have been removed using a flexible surface.

A flexible surface is calculated using a noise resilient level-set algorithm that is initialized on a face of the cuboid and is moved inwards plane by plane. Each pixel on the surface can proceed until it collides with the object based on intensity values. Once a pixel stops proceeding it creates a force field that, limits the progress of neighboring pixels by a set threshold, thus enabling the surface to wrap the object in a flexible manner, but not penetrate deeply into craters or holes. Noise artifacts are eliminated by allowing the surface to skip over a small island of object like tissue. The outside is defined as the volume between the initial and final surfaces.

The cuboid $C_d$ is restricted, further by clipping off all voxels posterior to the plane that separates the vertebral body from the spinal, canal using height analysis (See vertical line in FIG. 15, showing a lentiform shaped intervertebral disc, with a posterior bulge into the spinal canal which is removed from the disc region at the vertical line). The cuboid $C_d$ is also restricted by removing voxels above the superior cortex plane and below the inferior cortex plane, corresponding to the adjacent peaks in FIG. 13 (see illustration in FIG. 16, showing an intervertebral disc with superior and inferior planes orthogonal to the spinal canal polyline in the vicinity of the adjacent vertebral bodies' cortex).

Final intervertebral disc localization is accomplished by using a flood fill algorithm with 1-NN voting. The seed is selected by picking the rectangle Rsc located in the vertical center of the disc and extracting the rectangle's center point. The intensity threshold is defined in Equation (5).

$$\text{Threshold} = \text{Min}[100\ hu, \text{Mean}(R(SC)) + 2*\text{STDP}(R(SC))] \quad (5)$$

The localization result is illustrated in FIG. 17, showing the intervertebral discs marked in white in a sagittal max intensity projection. Note that for osteoporosis research the goal of intervertebral disc localization is to create markers for vertebral body segmentation. Therefore, non-skeletal regions, exterior to the disc, that are labeled as disc have low significance (e.g. disc herniation or algorithm inaccuracies). These regions are partially reduced using flexible surfaces.

Locating the Planes of the Intervertebral Discs

For each point in the plot shown in FIG. 13, a moving average, moving maximum, and moving minimum are calculated for a moving window typical of the height of a vertebra and its adjacent discs (e.g. 40 mm). See graph of FIG. 28, which illustrates the results of a statistical analysis to detect intervertebral disc planes. In the figure a depression in the weighted bone count between two elevations indicates a disc and the cortex of its adjacent vertebrae. See arrow in FIG. 28.

Next, each weight is assigned the first appropriate classification from the following list:

Extreme Spike: weights over a multiple (e.g. 60%) of the moving maximum.
Spike: weights over a multiple (e.g. 33%) of the moving Maximum.
High: weights over a multiple (e.g. double) of the moving average.
Min: weights at the moving minimum with a small threshold (e.g. 1).
Depression: weights below a threshold (e.g. 5) above the moving minimum.
Above average: weights over the moving average.
Below average: weights that do not fall into any of the classifications above.

Then, the complete set of weights is evaluated with each of the rules below in the order listed. After each rule is evaluated, a gap analysis is performed to locate suspect, missing discs, identified by gaps between discs that exceed a threshold (e.g. 150% of the average gap between discs in their neighborhood or 75% from image border for end discs). The rule set is executed repeatedly, until no new discs are detected.

Rule ES-M: a minimum between 2 close spikes or extreme spikes identifies a disc. However, if two-discs are identified close to each other (e.g. within 40% of the moving window), the wider of the two does not identify a disc (e.g. width measured as the distance between the spikes).

Rule ES-MD: in the vicinity of a missing disc, a narrow depression or min between 2 close spikes or extreme spikes identifies a disc.

Rule ESH-MD: in the vicinity of a missing disc, a narrow depression or min between 2 close spikes or extreme spikes or highs identifies a disc.

Rule ESHA-M: in the vicinity of a missing disc, a narrow min between 2 close spikes or extreme spikes, highs, or above averages identifies a disc.

Rule ESHA-MD: in the vicinity of a missing disc, a narrow min or depression between 2 close spikes or extreme spikes, highs, or above averages identifies a disc.

Rule ES-MDB: in the vicinity of a missing disc, a narrow below average, depression or min between 2 close spikes or extreme spikes identifies a disc.

Rule ES-MDBA: in the vicinity of a missing disc, a narrow min, depression, below or above average between 2 close spikes or extreme spikes identifies a disc.

Rule ESH-MDB: in the vicinity of a missing disc, a narrow min, depression, or below average between 2 close spikes or extreme spikes or highs identifies a disc.

Rule ESH-MDBA: in the vicinity of a missing disc, a narrow min, depression, below or above average between 2 close spikes or extreme spikes or highs identifies a disc.

Rule E-SHMDBA: in the vicinity of a missing disc, a narrow min, depression, below, above average, highs, or spikes between 2 extreme spikes identifies a disc, Rule ESH-MDBA-End: in the vicinity of a missing end disc, a narrow min, depression, below or above average at the end by a close spike or high identifies a disc.

The plane corresponding to the center of a depression identified as a disc, using these rules, is a disc plane.

Vertebral Body Segmentation System

FIG. 18 describes the workflow of the vertebral body segmentation system that delineates the trabecular bone and cortex of each vertebral body.

Vertebral Body Cortex Segmentation Component

Using the intervertebral discs as markers, a parallel axes cuboid $C_v$ is created encasing each pair of adjacent discs with an additional posterior and anterior margin (see white box in FIG. 19). $C_v$ is restricted by clipping off the voxels above the superior disc bisector plane and below the inferior disc bisector plane (see slanted lines in FIG. 19, showing the cuboid region encasing vertebra and both adjacent disks with posterior and anterior margins). $C_v$ is also restricted by attaching flexible surfaces to the superior, inferior, left, right, and anterior of the vertebral body (identified by densities typical of the cortex) and removing all voxels outside these surfaces.

$C_v$ is restricted posteriorly by removing all voxels that are part of the spinal canal (using a flood fill algorithm) and by clipping off all voxels posterior to the plane that hosts both the nearest segment of the spinal canal polyline and the X-axis. Further restriction of $C_v$ is achieved by attaching a flexible surface posterior to the vertebral body (identified by densities typical of the cortex) and removing all voxels outside this surface.

The resulting restricted region in some cases may still include structures that abut the vertebral body. This problem typically occurs due to contrast in the vascular or digestive systems or vascular calcifications (see FIG. 20, a CT demonstrating calcification in the aorta in the vicinity of the vertebral body). To resolve this problem we apply a connectivity algorithm to remove exterior structures: a line is extended from each voxel in the region to the estimated vertebra center and only voxels on the line segment between the center and the first intersection with a boundary are identified as vertebral body. Note that in some cases osteophytes, which are typically not significant for the diagnosis of osteoporosis, may be partially removed by this algorithm. Finally, a 1-NN voting flood fill algorithm is used to remove any remaining protuberances. The result is the vertebral body region $R_v$, shown in FIG. 21, two three-dimensional views of vertebra region Rv in its cuboid region Cv (wireframe) after restricted voxels are removed.

After the vertebral body region $R_v$ is determined, the cortex, is identified using axes parallel ray tracing starting from each of the six sides of cuboid $C_v$ and labeling voxels with cortex intensity on the outer shell of $R_v$.

Vertebral Body Trabecular Bone Segmentation Component

To label the trabecular bone inside $R_v$ while avoiding leakage through cortex discontinuities, a 1-NN voting flood fill algorithm is employed. A set of seeds are located based on common anatomical dimensions and the intensity is set to below the minimum threshold of the cortex. Next all unlabeled voxels within a cuboid encasing the cortex that have intensities higher or equal to the same threshold are also labeled as trabecular bone. Finally, an iterative hole-filling algorithm fills small unlabeled regions inside the trabecular bone.

Segmentation Error Correction Component

After applying the algorithm above, small external structures marked as cortex may still remain as shown in FIGS. 22(a) and 22(b) (e.g. due to vascular calcification in close proximity to the vertebral, body), FIGS. 22(a) and (b) show samples of islands marked as cortex in a label map of cortex and trabecular bone. To resolve this problem, a 1-NN voting flood fill algorithm on the unified label map of the cortex and trabecular bone removes islands including islands connected to the main vertebral body over narrow bridges.

Due to anatomical abnormalities, the proceeding components may label voxels in the spinal canal as trabecular bone. This is typical in cases where the posterior cortex is extremely thin or partially missing due to epidural veins. To resolve this problem, a flexible surface is attached to the posterior of the label map using the labels of the cortex to identify the object. AH voxels outside this surface are removed.

Segmentation Results

The methodology described above results in the segmentation of the vertebral body cortex and trabecular bone. This segmentation can be used to detect findings of osteoporosis by analyzing vertebral body morphology and bone density and structure.

Experimentation and Validation
Experimentation Methods

The methodology described in this paper has been implemented in C++ using Microsoft Visual Studio and the ITK segmentation and registration toolkit, on Microsoft Windows 7, 64-bit OS. In the initial stage, the program analyzed 1,044 CT studies with slice thickness ≤1 mm containing a total of 8,080 complete vertebrae. The CT archive originated from 15 sites in 11 states and the principal reason for the imaging was virtual colonoscopy screening. The full set included 1,080 CT studies of the abdomen and pelvis, however, 12 were manually excluded due to acquisition errors (e.g. orientation miss alignment) and 24 were automatically excluded due to lateral decubitus patient position, which is unsupported by our imaging acquisition system, leaving a total, of 1,044 CT studies from 520 patients, in 85% of the studies the age was recorded and was in the range of 50-110 years ($\mu$=62 Y, $\sigma$=13.8 Y). 50.4% of the studies were performed with the patient in the prone position and 49.6% in the supine position. In 89% of the studies gender was recorded with a distribution of 47% males and 53% females.

Validation of results was performed by two observers: (A) an engineer specializing in medical informatics validated all 8,080 vertebral bodies included in the 1,044 studies and (B) a board certified diagnostic radiologist validated 773 vertebral bodies in a random sample of 100 studies. The observers evaluated the following properties:

Vertebral Body Defection

For each of the 1,044 studies, the number of detected, undetected and false positives was recorded. Detection was determined by inspecting representative sagittal reconstructed images and verifying that the center of gravity of the segmentation is inside the vertebral body, in a location, where trabecular bone density can be sampled as demonstrated in FIG. 23 (Vertebral bodies that were partially outside the image were excluded). FIG. 1 shows a vertebra, center: (a) detected—marked with a white cross, (b) undetected, and (e) false positive—marked with a white cross.

Vertebral Body Morphology Segmentation

For each of the 1,044 studies, the number of correct and incorrect morphological segmentations was recorded. A mid sagittal reconstructed image was inspected for cortex segmentation adequate to measure vertebral heights at the anterior, central, and posterior aspects to detect vertebral fractures using morphology analysis techniques referenced in the introduction. Where cortex segmentation was not adequate to measure heights, the trabecular bone segmentation was inspected as well. Each vertebra received a pass/fail score as shown in FIG. 24, which shows cortex morphology segmentation marked with white dots: (a) pass, (b) fail. For this inspection the observer viewed the mid sagittal, reconstruction of the CT study, with an overlay of the segmentation outline, as shown by the dotted contour, and answered the question: "Do the vertebral, body heights of the segmentation adequately represent the heights in the CT study to enable the accurate measurement of vertebral fractures?" Small isolated segmentation errors in the vicinity of the intervertebral disc were usually ignored unless they could impair the measurements of the heights. Posterior and anterior errors that do not impact height measurement were also disregarded. In cases where the mid sagittal plane displayed incomplete results other sagittal planes were inspected as well (e.g. due to scoliosis or patient's body tilt). In cases where the significance of segmentation errors on height measurements was uncertain, additional images were inspected including multiple 3D label map projections superimposed over of the CT study using NA-MIC 3DSlicer visualisation tools.

Multi Plane Vertebral Body Morphology Segmentation

In a sample of 219 CT studies, 1,641 vertebrae were evaluated at 3 sagittal planes and 5 coronal planes as shown in FIG. 25, showing multi-plane vertebral body morphology segmentation denoted with white dotted outlines: (a) right, sagittal plane, (b) mid sagittal plane, (c) left sagittal plane, (d) anterior coronal plane, (e) mid-anterior coronal plane, (f) mid coronal plane, (g) mid-posterior coronal plane, (h) posterior coronal plane with epidural vein marked with an arrow. The studies were selected by adding 119 randomly selected CT studies to the 100 CT study sample set validated by observer B as noted in 0. Observer A analyzed the 8 planes of each of the 1,641 vertebrae and graded each of the resulting 13,128 images with either a pass or fad using the same height measurement criteria used for the regular vertebral body morphology segmentation described in 0. In eases where a coronal plane fell on a posterior region of the vertebral body including a prominent epidural vein, the plane was excluded from the evaluation (see FIG. 25(h)).

Execution Time

Program execution time was measured by recording process tick count for the analysis of each study running on a Lenovo ThinkStation S20 (Intel Xeon W3550 3.06 GHz 1066 MHz 8 MB L2, 6 GB ECC DDR3 PC3-10600 SDRAM, priced at approx. 1,500 USD).

Data Analysis

All results were stored in a Microsoft Access database and statistics were performed using Microsoft Access and Microsoft Excel Interobserver agreements were calculated using the following equations:

$$\text{Detection Agreement} = \frac{1}{N}\sum_{N=1}^{N}\frac{\text{Abs}(U_{KA} - U_{KB})}{n_K} \quad (6)$$

$$\text{FP Agreement} = \frac{1}{N}\sum_{K=1}^{N}\frac{\text{Abs}(FP_{KA} - FP_{KB})}{n_K} \quad (7)$$

$$\text{Segmentation Agreement} = \frac{1}{N}\sum_{K=1}^{N}\frac{\text{Abs}(MF_{KA} - MF_{KB})}{n_K - U_{KB}} \quad (8)$$

where:
N—number of CT studies validated by both observers.
$U_{KA}$, $U_{KB}$—number of undetected vertebrae in study K as noted by observers A, B.
$n_K$—number of complete vertebrae in study K as noted by observer 8
$FP_{KA}$, $FP_{KB}$—number of false positives in study K as noted by observers A, B.
$MF_{KA}$, $MF_{KB}$—number of failed morphology segmentations in study K as noted by observers A, B.

Results

Vertebral Body Detection

TABLE 2

Vertebral body detection results

| | Observer | Total Vertebrae | Detected Vertebrae | Missed Vertebrae | False Positives |
|---|---|---|---|---|---|
| 1,044 CT studies | A (engineer) | 8,080 | 7,777 (96.25%) | 303 (3.75%) | 80 (1%) |
| Sample 100 CT studies | A (engineer) | 733 | 750 (97%) | 23 (3%) | 6 (0.8%) |
| | B (radiologist) | | 750 (97%) | 23 (3%) | 6 (0.8%) |
| | Interobserver agreement | | 100% | | 100% |

Table 2 summarizes the validation results for vertebral body detection, showing an overall detection rate of 96.25% and FP rate of 1% in the 8,080 vertebrae of the complete set of 1,044 CT studies. There was a 100% interobserver agreement on a sample. For osteoporosis screening based on trabecular bone analysis, this detection rate is sufficient. Of concern is the 1% false positive rate and further research is required to find methods to automatically preclude these cases.

Vertebral Body Morphology Segmentation

TABLE 3

Vertebral body morphology segmentation results

| | Observer | Total Vertebrae | Correct Segmentation | Incorrect Segmentation |
|---|---|---|---|---|
| 1,044 CT studies | A (engineer) | 7,777 | 6,477 (83.3%) | 1,300 (16.7%) |
| Sample 100 CT studies | A (engineer) | 750 | 608 (81%) | 142 (19%) |
| | B (radiologist) | | 602 (80.3%) | 148 (19.7%) |
| | Interobserver agreement | | 96.1% | |

Table 3 summarizes the validation results of vertebral body morphology segmentation, showing an 83.3% success rate in 7,777 vertebrae with interobserver agreement of 96.1% on a sample. To reduce potential false positives in osteoporosis detection resulting from the 16.7% incorrect segmentations, further research is required to find methods to automatically preclude these cases.

Multi Plane Vertebral Body Morphology Segmentation

TABLE 4

Multi plane vertebral body morphology segmentation results

| Number CT studies | 219 | |
|---|---|---|
| Total vertebrae | 1641 | |
| Vertebral body morphology segmentation | Pass 83.1%/ Fail 16.9% | |
| Multi plane Vertebral body morphology segmentations: | 3 Sagittal planes | 5 Coronal planes |
| % vertebrae with no planes segmented incorrectly | 72.8% | 75.5% |
| % vertebrae with up to 1 plane segmented incorrectly | 81.6% | 82.3% |
| % vertebrae with up to 2 planes segmented incorrectly | 85.4% | 86.8% |
| % vertebrae with up to 3 or more planes segmented incorrectly | 14.6% | 13.2% |

Table 4 summarizes the segmentation success and failure rates for 1,641 vertebrae in a random sample of 219 CT studies when inspecting the morphology on multiple sagittal and coronal planes. The regular vertebral body morphology segmentation described in 0 for this sample has an 83.1% success/16.9% failure rate. Evaluating 3 sagittal planes per vertebra found that only 72.8% had errors in none; however, when requiring only one sagittal plane have correct segmentation the results improved to 85.4% success/14.6% failure, presenting a 2.3% improvement over the regular segmentation. This finding encourages further research into techniques that can automatically select the best sagittal plane for height analysis. The results also demonstrate that coronal planes have a higher segmentation success rate than sagittal planes prompting research into the use of coronal planes for vertebral height analysis. Coronal plane analysis is also less sensitive to segmentation errors when detecting osteoporotic fractures.

Processing Time

The processing time for each study when reading from axial DICOM files was 75-439 seconds (μ250 s, σ=50 s, N=381). For studies that were cropped and cached on disc in advance as a single MHA file, the processing time was 90-458 seconds (μ=1.92 s, σ=50 s, N=663) saving approximately a minute consumed mostly by loading hundreds of DICOM files.

In scenarios that allow preprocessing before and during diagnosis by a radiologist, this timing will typically not introduce delays to the clinical workflow. In the mass screening scenario 10,000 studies will require approximately 3 days when reading from DICOM files using 10 machines comparable with the one described in the methods section. Time may be reduced by adding hardware or using a hosted service.

Resiliency To Abnormalities

A unique attribute of our research is redundancies and special treatment accounting for a broad range of anatomical and study variation typical of vertebral imaging studies, specifically those common in older population who are the target for osteoporosis screening. FIG. 26 demonstrates examples where the algorithm succeeds in spite of abnormalities; (a) calcification of the aorta, (b) epidural vein, (c) osteophytes, (d) narrow disc with vacuum phenomenon, (e) vertebral fracture, (f) scoliosis, (g) contrast in colon, (h) endplate irregularity, (i) schmorl nodes, (j) calcified anterior longitudinal ligament. However, as shown in FIG. 27, in some eases abnormalities may lead to failure of the algorithm. FIG. 27 shows image variation failure samples: (a) aorta calcification mistaken as cortex, (b) metal screws cause incorrect segmentation), (c1) and (c2) disc calcification causes incorrect segmentation, (d) calcified anterior longitudinal ligament causes incorrect segmentation, (e) incorrect segmentation of fractured vertebral body, (f) spondylolisthesis causing detection failure.

Comparison with Known Research
Comparison of Results

Our study is unique in terms of using a large multi-center sample set and success metrics specific to osteoporosis. This creates obstacles when attempting to compare results with references. The two papers with results that can be partially compared are listed below.

Klinder et al. [17] reports a detection rate of 92% on 64 CT studies as compared to our 96.25% detection rate on 1,044 CT studies. In Klinder's study, 95% of the detected vertebrae had a mean point-to-surface segmentation error of 1.12±1.04 mm. As our segmentation success metric relates to vertebral body height measurements, there is insufficient data to compare the segmentation results.

Asian et al [22] reports excellent segmentation in 64.1% of vertebrae in 30 CT studies and 20.5% good segmentation containing small areas of disc or adjacent vertebrae viewed on an axial slice. It is not clear how these errors would map to our metrics and what portion of the good segmentations would be adequate for vertebral body height measurements.

Comparison of Methodologies

Our segmentation approach as depicted in FIG. 2, initiates the search from the posterior, locating the spinous processes, the canal, and the discs and only then segmenting the vertebral bodies. This approach successfully addresses variations in protocol and in anatomy typical of the age group susceptible to osteoporosis. Similarly, Klinder et al. [17] seek the spinal canal first and report resiliency to anatomical and protocol variations on a 64 CT sample, Yiebin et al. [23] also seek the spinal canal and then find the intervertebral discs, using ray tracing from the anterior of vertebral bodies, and report resiliency to some calcifications but do not address contrast. Other papers [12, 13, 19, 20, 21, 22] approach the segmentation problem on the axial plane and do not clearly address these anatomical and protocol variations. Our own attempts in analyzing the axial, planes encountered obstacles when treating anatomical and protocol variations, and we concluded that the approach from the posterior yields better results.

Other differentiators of our research, include entropy analysis for scanner artifact removal, use of noise resistant flexible surfaces to restrict the vertebral bodies, and special treatment for high density structures dial abut the vertebral body. The combination of these methods produces segmentation results that exceed those of other methodologies when, addressing the osteoporosis scenario.

The present invention provides a fully automated vertebral body segmentation process as a building block for an automated osteoporosis screening application. The method was tested on a large set of 1,044 abdominal CT studies performed for the purpose of virtual colonoscopy in a multicenter study on patients in the age group susceptible to osteoporosis. The segmentation results were validated by a board certified radiologist and by an engineer specializing in medical informatics, using criteria relevant to morphology and bone structure analysis, and produced good results, overcoming many cases of anatomical variations, abnormalities, and study and protocol variations.

REFERENCES

[1] US General Surgeon, "The 2004 Surgeon General's Report on Bone Health and Osteoporosis," 2004.
[2] International Osteoporosis Foundation, "Facts and statistics about osteoporosis and its impact".
[3] J. E. Lafata, D. Kolk, E. L. Peterson, B. D. McCarthy, T. W. Weiss, Y. T. Chen and B. K. Muma, "Improving Osteoporosis Screening: Results from a Randomized Cluster Trial," 2007.
[4] Y. Masharawi, B. Rothschild, N. Peled and I. Hershkovitz, "A simple radiological method for recognizing osteoporotic thoracic vertebral compression fractures and distinguishing them from Scheuermann disease," vol. 34, 2009.
[5] H. K. Genant, C. Y. Wu, C. Van Kuijk and M. C. Nevitt, "Vertebral Fracture Assessment Using a Semiquantitative Technique," vol. 8, 1993.
[6] F. Grades, C. Roux, M. C. de Vernejoul, G. Utard, J. L. Sebert and P. Fardellone, "Comparison of Four Morphometric Definitions and a Semiquantitative Consensus Reading for Assessing Prevalent Vertebral Fractures," vol. 12, 2001.
[7] G. Guglielmi, L. P. Stoppino, M. J. Placentino, F. D'Errico and F. Palmieri, "Reproducibility of a semi-automatic method for 6-point vertebral, morphometry in a multi-centre trial," vol. 69, 2009.
[8] F. Grados, J. Fechtenbaum, E. Flipon, S. Kolta, C. Roux and P. Fardellone, "Radiographic methods for evaluating osteoporotic vertebral fractures," vol. 76, 2009.
[9] A. Guermazi, A. Mohr, M. Grigorian, B. Taouli and H. K. Genant. "Identification of vertebral fractures in osteoporosis," 2002.
[10] T. M. Link, B. B. Koppers, T. Licht, J. Bauer, Y. Lu and E. J. Rummeny, "In vitro and in vivo spiral CT to determine bone mineral density-initial, experience in patients at risk for osteoporosis," vol. 231, 2004.
[11] H. K. Genant, K. Engelke and S. Prevrhal, "Advanced CT bone imaging in osteoporosis," vol. 47, 2008.
[12] S. Nishihara, H. Fujita, T. Iida, A. Takigawa, T. Hara and X. Zhou, "A basic study for automatic recognition of osteoporosis using, abdominal X-ray CT images," vol. 5370, 2004.
[13] S. Nishihara, H. Fujita, T. Iida, A. Takigawa, T. Hara and X. Zhou, "Evaluation of osteoporosis in X-ray CT examination: A preliminary study for an automatic recognition algorithm for the central part of a vertebral body using abdominal X-ray CT images," vol. 29, 2005,

[14] D. Müller. J. S. Bauer, M. Zeile, E. J. Rummeny and T. M. Link, "Significance of sagittal reformations in routine thoracic and abdominal multislice CT studies for detecting osteoporotic fractures and other spine abnormalities," 2008.

[15] T. Bartalena, M. F. Rinaldi, C. Modolon, L. Braccaioli, N. Sverzellati, G. Rossi, E. Rimondi, M. Busacca, U. Albisinni and D. Resnick, "incidental vertebral compression fractures in imaging studies—Lessons not learned by radiologists," 2010.

[16] A. L. Williams, A. Al-Busaidi. P. J. Sparrow, J. E. Adams and R. W. Whitehouse, "Under-reporting of osteoporotic vertebral fractures on computed tomography," no. 69, 2009.

[17] T. Klinder, J. Ostermann, M. Ehmb, A. Franz, R. Kneser and C. Lorenz, "Automated model-based vertebra detection, identification, and segmentation in CT images," vol. 13, 2009.

[18] M. S. Asian, A. Ali, A. A. Farag, B. Arnold, D. Chen and P. Xiang, "3D Vertebrae Segmentation in CT Images with Random Noises," 2010.

[19] P. I. Saparin, W. Gowin, J. Kurths and D. Felsenberg, "Measures of complexity and processing of vertebral CT-images," Chicago, Ill., 1997.

[20] M. S. Asian, A. Ali, A. A. Farag. H. Kara, B. Arnold and P. Xiang, "3D Vertebral Body Segmentation Using Shape Based Graph Cuts," Istanbul 2010.

[21] H. Li and Z. Wang, "A Seepage Flow Model for Vertebra CT image Segmentation," 2006,

[22] M. S. Asian, A. Ali, H. Rara and A. A. Farag, "An automated vertebra identification and segmentation in CT images." Hong Kong, 2010,

[23] K. Yiebin and K. Dongsung, "A fully automatic vertebra segmentation method using 3D deformable fences," *Computerized Medical imaging and Graphics*, vol. 33, p. 343-352, 2009.

[24] T. Kapur. S. Pieper, R. Whitaker, S. Aylward, M. Jakab, W. Schroeder and R. Kikinis, "The National Alliance for Medical image Computing, a roadmap initiative to build a free and open source software infrastructure for translational research in medical image analysis," *JAMIA*. 2011.

What is claimed:

1. A method performed in a computer system comprising the steps of:
    receiving as an input a digital representation of an image of a volume region of a patient's body containing the spine;
    using at least one of statistical and heuristic computational techniques on the digital representation, isolating the spine from the surrounding volume, and in the spine, segmenting the vertebral body trabecular bones, the vertebral body cortexes, and the intervertebral discs, and locating the planes of the intervertebral discs;
    wherein segmenting the intervertebral discs includes steps (i) and (ii):
        (i) positioning a rectangular parametric curve along the expected center of a vertebral body; and
        (ii) inspecting a cross section of the parametric curve; and
    creating a graph of weight as a function of position along the spine; and
    generating a map corresponding to the volume containing plural elements wherein each element is identified as background or as part of a specified part of the spine.

2. The method of claim 1 wherein the step of locating the planes of the intervertebral discs comprises the step of, for each point in the graph, calculating a moving average, moving maximum, and moving minimum for a moving window typical of the height of a vertebra and its adjacent discs.

3. The method of claim 2 further comprising assigning each weight the first appropriate classification from the following list:
    Extreme Spike: weights over a multiple of the moving maximum;
    Spike: weights over a multiple of the moving maximum;
    High: weights over a multiple of the moving average;
    Min: weights at the moving minimum with a small threshold;
    Depression: weights below a threshold above the moving minimum;
    Above average: weights over the moving average;
    Below average: weights that do not fall into any of the classifications above.

4. The method of claim 3, further comprising evaluating the weights with each of the rules below in the order listed:
    Rule ES-M: a minimum between 2 close spikes or extreme spikes identifies a disc, however, if two discs are identified close to each other, the wider of the two does not identify a disc;
    Rule ES-MD: in the vicinity of a missing disc, a narrow depression or min between 2 close spikes or extreme spikes identifies a disc;
    Rule ESH-MD: in the vicinity of a missing disc, a narrow depression or min between 2 close spikes or extreme spikes or highs identifies a disc;
    Rule ESHA-M: in the vicinity of a missing disc, a narrow min between 2 close spikes or extreme spikes, highs, or above averages identifies a disc;
    Rule ESHA-MD: in the vicinity of a missing disc, a narrow min or depression between 2 close spikes or extreme spikes, highs, or above averages identifies a disc;
    Rule ES-MDB: in the vicinity of a missing disc, a narrow below average, depression or min between 2 close spikes or extreme spikes identifies a disc;
    Rule ES-MDBA: in the vicinity of a missing disc, a narrow min, depression, below or above average between 2 close spikes or extreme spikes identifies a disc;
    Rule ESH-MDB: in the vicinity of a missing disc, a narrow min, depression, or below average between 2 close spikes or extreme spikes or highs identifies a disc;
    Rule ESH-MDBA: in the vicinity of a missing disc, a narrow min, depression, below or above average between 2 close spikes or extreme spikes or highs identifies a disc;
    Rule E-SHMDBA: in the vicinity of a missing disc, a narrow min, depression, below, above average, highs, or spikes between 2 extreme spikes identifies a disc;
    Rule ESH-MDBA-End: in the vicinity of a missing end disc, a narrow min, depression, below or above average at the end by a close spike or high identifies a disc.

5. The method of claim 4 wherein, after each rule is evaluated, a gap analysis is performed to locate suspect missing discs, identified by gaps between discs that exceed a threshold.

6. The method of claim 4 wherein the rule set is executed repeatedly, until no new discs are detected.

7. The method of claim 1 further comprising calculating a weight using an additive combination of medium density and high density components.

* * * * *